US012178650B2

(12) United States Patent
Rouet et al.

(10) Patent No.: US 12,178,650 B2
(45) Date of Patent: Dec. 31, 2024

(54) SYSTEMS AND METHODS FOR GUIDING THE ACQUISITION OF AN ULTRASOUND IMAGE

(71) Applicant: KONINKLIJKE PHILIPS N.V., Eindhoven (NL)

(72) Inventors: Laurence Rouet, Paris (FR); Cybèle Ciofolo-Veit, Meudon (FR); Thierry Lefevre, Suresnes (FR); Caroline Denise Francoise Raynaud, Paris (FR); Cristian Lorenz, Hamburg (DE); Tobias Klinder, Uelzen (DE); Nicole Schadewaldt, Nortdrstedt (DE); Alexander Schmidt-Richberg, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 931 days.

(21) Appl. No.: 17/285,379

(22) PCT Filed: Oct. 14, 2019

(86) PCT No.: PCT/EP2019/077752
§ 371 (c)(1),
(2) Date: Apr. 14, 2021

(87) PCT Pub. No.: WO2020/078889
PCT Pub. Date: Apr. 23, 2020

(65) Prior Publication Data

US 2021/0338203 A1 Nov. 4, 2021

(30) Foreign Application Priority Data

Oct. 15, 2018 (EP) .................................... 18290118

(51) Int. Cl.
*A61B 8/00* (2006.01)
*A61B 8/08* (2006.01)

(52) U.S. Cl.
CPC ............ *A61B 8/483* (2013.01); *A61B 8/0866* (2013.01); *A61B 8/4245* (2013.01); *A61B 8/523* (2013.01)

(58) Field of Classification Search
CPC ... A61B 8/0866; A61B 8/4245; A61B 8/5215; A61B 8/523
See application file for complete search history.

(56) References Cited

U.S. PATENT DOCUMENTS 5,997,479 A 12/1999 Savord
6,013,032 A 1/2000 Savord
(Continued)

FOREIGN PATENT DOCUMENTS

WO 2018060723 A1 4/2018

OTHER PUBLICATIONS

International Search Report and Written Opinion of PCT/EP2019/077752 dated Feb. 12, 2020.
(Continued)

*Primary Examiner* — Rajeev P Siripurapu

(57) ABSTRACT

The invention provides a method for guiding the acquisition of an ultrasound image. A 3D ultrasound image is acquired by an ultrasound probe at a first position and an anatomical structure is identified within the 3D ultrasound image. A target imaging plane is estimated based on the identified anatomical structure and it is determined whether the target imaging plane is present within the 3D ultrasound image. If the target imaging plane is present, a displacement between a central plane of the 3D ultrasound image and the target plane is determined. If the displacement is below a predetermined threshold, the target imaging plane is extracted and
(Continued)

if the displacement is above the predetermined threshold, an instruction to acquire a 3D ultrasound image with the ultrasound probe at a second position, different from the first position, is generated based on the displacement. The invention further provides a method for estimating a target imaging plane. A central plane of a 3D ultrasound image is obtained, wherein the central plane contains at least part of an anatomical structure and abounding box is generated around the anatomical structure. The bounding box is divided into a grid having a plurality of grid points and, for each grid point; an offset is estimated between the central plane and the target imaging plane. Finally, coordinates of the target imaging plane are estimated based on the offset for each grid point of the bounding box.

15 Claims, 7 Drawing Sheets

(56) References Cited

U.S. PATENT DOCUMENTS 6,283,919 B1 9/2001 Roundhill
6,443,896 B1 9/2002 Detmer
6,458,083 B1 10/2002 Jago
6,530,885 B1 3/2003 Entrekin
6,623,432 B2 9/2003 Powers
8,805,047 B2 8/2014 Ma
2007/0081705 A1* 4/2007 Carneiro ............ G06F 18/2321 382/128
2009/0093717 A1 4/2009 Carneiro
2016/0038122 A1 2/2016 Lee
2016/0361045 A1 12/2016 Yoo
2017/0007208 A1 1/2017 Deng

OTHER PUBLICATIONS

Redmon, Joseph et al "YOLO9000: Better, Faster, Stronger", 2017 IEEE Conference on Computer Vision and Pattern Recognition.
Pan, S.J. et al A Survey on Transfer Learning, IEEE Trans. Knowledge Data Eng. vol. 22, No. 10, pp. 1345-1359, 2009.
Schmidt-Richberg et al "Abdomen Segmenation in 3D Fetal Ultrasound Using CNN-Powered Deformable Models", MICCAI Workshop on Fetal and Infant Imaging 2017—Abstract only.
Brosch, T. et al "Foveal Fully Convolutional Nets for Multi-Organ Segmentation", Proc. SPIE, 10574U, 2018.
Papageorghiou, A.T. et al. International standards for fetal growth based on serial ultrasound measurements: the Fetal Growth Longitudinal Study of the Intergrowth-21st Project, The Lancet 384, pp. 869-879, 2014.
Lu, Xiaguang et al "AUTOMPR: Automatic Detection of Standard Planes in 3D Echocardiography", 2008.
Zheng, Yefeng et al "Robust Landmark Detection in Volumetric Data with Efficient 3D Deep Learning", Medical Maging Technologies, Computer Science, 2017.
Sofka, Michal et al Automatic Detection and Measurment of Structures in Fetal Head Ultrasound Volumes using Sequential Estimation and Integrated Detection Network (IDN), IEEE Transactions on Medical Imaging, vol. 33, No. 5, May 2014.
Erhan, Dumitru et al "Scalable Object Detection using Deep Neural Networks", 2014 IEEE Conference on Computer Vision and Pattern Recognition.
Baumgartner, C.F. et al "Real-Time Standard Scan Plane Detection and Localisation in Fetal Ultrasound using Fully Convolutional Neural Networks", International Conf. on Medical Image Computing and Computer-Assisted Intervention MICCAI 2016.
Li, Yuanwei et al "Standard Plane Localisation in 3D Fetal Ultrasound using Network with Geometric and Image Loss", 1st Conf. on Medical Imaging With Deep Learning (MIDL 2018).

* cited by examiner

SYSTEMS AND METHODS FOR GUIDING THE ACQUISITION OF AN ULTRASOUND IMAGE

This application is the U.S. National Phase application under 35 U.S.C. § 371 of International Application No. PCT/EP2019/077752, filed on Oct. 14, 2019, which claims the benefit of European Patent Application 18290118.1 filed Oct. 15, 2018. These applications are hereby incorporated by reference herein.

FIELD OF THE INVENTION

The present invention relates to the field of ultrasound imaging, and more specifically to the field of guided ultrasound imaging.

BACKGROUND OF THE INVENTION

Ultrasound imaging is the modality of choice for fetal screening, as well as many other non-invasive medical examinations, as it is able to render fetal anatomy in sufficient detail, while at the same being time and cost effective with no known adverse effects. Fetal screening covers a variety of fetal growth measures, but also the detection of fetal abnormalities. A major part of the examinations start at 18 to 22 weeks gestational age (GA) with specific recommended standard measurements.

Typically, fetal screening exams are performed using 2D ultrasound images. Obtaining the correct views requires advanced training and is mostly performed by expert users. Due to the lack of expert resources, especially in remote areas, it is not always possible to offer ultrasound fetal screening. For untrained sonographers, acquiring the standard clinical planes and structures of interest, which are used to perform manual or automatic biometry measurements that are necessary for fetal growth evaluation, can be challenging.

Typically, a set of anatomically defined planes of the fetal head, thorax and abdomen are acquired and examined. For 3D US images, the automatic selection of 2D planes for standard biometry measurements is a major challenge. For example, the abdominal circumference (AC) is a standard measurement to estimate fetal size and growth. Detailed screening guidelines define criteria that the scan plane must meet in order to enable valid biometry measurement. For example: the stomach and umbilical vein must be visible while heart or kidney should not; the scan plane should be orthogonal to the head-to-toe axis; and the shape of the abdomen should be as round as possible.

Document US 2016/361045 A1 relates to an ultrasonic imaging apparatus and a control method thereof. The ultrasonic imaging apparatus includes an acquisition unit configured to acquire a volume data of an object and a process configured to determine whether an acquisition position of the volume data is within an allowable range by using pre-stored landmark information, and further configured to acquire a plurality of reference planes from the volume data when the acquisition position of the volume data is within the allowable range.

In addition, in US 2017/007208 A1 it is disclosed a technique for improving the imaging quality of a desired imaging plane in the volume of interest of a subject, in which it is possible to directly scan the desired imaging plane by exploiting the capability of a 2D matrix ultrasound transducer and/or the flexibility of the position/orientation of the ultrasound probe, rather than reconstructing the image of the desired imaging plane by interpolation of the ultrasound echo data of the plurality of scanning planes.

There is therefore a need for an ultrasound imaging method that simplifies or automates the acquisition of the required standard clinical planes without requiring significant additional hardware.

SUMMARY OF THE INVENTION

The invention is defined by the claims.

According to examples in accordance with an aspect of the invention, there is provided a method for guiding the acquisition of an ultrasound image, the method comprising:

- acquiring a 3D ultrasound image by controlling an ultrasound probe at a first position;
- identifying an anatomical structure within the 3D ultrasound image;
- estimating a target imaging plane based on the identified anatomical structure;
- determining if the target imaging plane is present within the 3D ultrasound image;
- if the target imaging plane is present, determining a displacement between a central plane of the 3D ultrasound image and the target plane; and
- if the displacement is below a predetermined threshold, extracting the target imaging plane from the 3D ultrasound image; or
- if the displacement is above the predetermined threshold, generating an instruction to acquire a 3D ultrasound image with the ultrasound probe at a second position, different from the first position, based on the displacement.

The method provides for a simplified acquisition of a target imaging plane.

The method begins with the acquisition of a 3D volume in the vicinity of a target imaging area. An anatomical structure is identified within the image and an associated target image plane is determined based on the identified structure.

If the target plane is within the 3D volume, the target plane may be automatically acquired without additional input from the user.

If the target plane is not within the 3D volume, the user is provided with instruction on how to move the probe to acquire a 3D volume that includes the target plane.

In this way, a user may be required only to move the ultrasound probe to the vicinity of a target area in order to acquire accurate target imaging planes needed for a clinical process. This reduces, or eliminates, the need for the user to perform complex manipulations of the probe in order to obtain the required images.

The above method includes the estimation of a target imaging plane. According to examples in accordance with an aspect of the invention, there is provided a method for estimating a target imaging plane, the method comprising:

- obtaining a central plane of the 3D ultrasound image, wherein the central plane contains at least part of the anatomical structure;
- generating a bounding box around the anatomical structure in the central plane;
- dividing the bounding box into a grid having a plurality of grid points;
- for each grid point of the plurality of grid points, estimating an offset between the central plane and the target imaging plane (e.g. an optimal imaging plane); and estimating coordinates of the target imaging plane based on the offset for each grid point of the bounding box.

This method of estimating a target imaging plane may be used in the context of guiding the acquisition of an ultrasound image; however, it may also be used in any other imaging context requiring the estimation of a target imaging plane.

This method provides for an improved method for acquiring a target image plane in a 3D ultrasound volume.

Typical image plane acquisition requires specific biometric data in order to navigate the volume to reach the required imaging plane. This method allows an imaging plane to be acquired directly, without requiring a search for all relevant structures within the 3D volume.

Rather, the target image plane is searched for directly using a set of offset values from a central image plane of the volume.

In an embodiment, the estimation of the offset comprises applying a multi-resolution neural network to the central plane.

In a further embodiment, the applying of the multi-resolution neural network comprises:

generating a first image patch from the central plane, wherein the first image patch has a first resolution;

generating a second image patch from the central plane, wherein the second image patch has a second resolution, lower than the first resolution;

extracting a first feature map from the first image patch and a second feature map from the second image patch;

combining the first feature map with the second feature map; and generating an output layer based on the combined maps, wherein the output layer comprises the offset for each grid point.

In this way, a series of convolutional layers may be used to generate the output layer holding the offsets required to reach the target plane from the central plane.

The offset grid has a far lower resolution than the original image. A typical method would require up-sampling between each consecutive layer. However, in this case, each layer of the network is downsampled from the previous one until the resolution of the bounding box grid is achieved.

In an arrangement, the identifying of the anatomical structure comprises segmenting the anatomical structure.

In this way, it is possible to accurately identify structures within the image.

In an arrangement, the displacement comprises one or more of:

a translation; and a rotation.

Thus, the user may be directed to capture a specific target plane in a clear and simple manner.

In an embodiment, the instruction comprises one or more of:

a visual instruction; and an audible instruction.

In this way, the user may receive the instruction in a manner according to their preference.

In an embodiment, the visual instruction comprises one or more of:

a schematic based instruction; and a 3D volume based instruction.

In an arrangement, the method further comprises performing biometric analysis on the acquired target imaging plane.

In this way, biometric analysis may be automatically performed on the acquired target plane without requiring further intervention from the user. Thus, the level of skill required by the user to perform the method may be further reduced.

According to examples in accordance with an aspect of the invention, there is provided a computer program comprising computer program code means which is adapted, when said computer program is run on an ultrasound imaging system, to implement the methods described above.

According to examples in accordance with an aspect of the invention, there is provided an ultrasound imaging system, the system comprising:

an ultrasound probe adapted to acquire a 3D ultrasound image when located at a first position;

a processor, wherein the processor is adapted to:

identify an anatomical structure within the 3D ultrasound image;

estimate a target imaging plane based on the identified anatomical structure;

determine if the target imaging plane is present within the 3D ultrasound image;

if the target imaging plane is present, determine a displacement between a central plane of the 3D ultrasound image and the target plane; and if the displacement is below a predetermined threshold, extract the target imaging plane from the 3D ultrasound image; or if the displacement is above the predetermined threshold, generate an instruction to acquire a 3D ultrasound image with the ultrasound probe at a second position, different from the first position, based on the displacement.

In an arrangement, the processor is further adapted to:

obtain a central plane of the 3D ultrasound image, wherein the central plane contains at least part of the anatomical structure;

generate a bounding box around the anatomical structure in the central plane;

divide the bounding box into a grid having a plurality of grid points;

for each grid point of the plurality of grid points, estimate an offset between the central plane and the target imaging plane; and estimate coordinates of the target imaging plane based on the offset for each grid point of the bounding box.

In a further arrangement, the processor is further adapted to apply a multi-resolution neural network to the central plane, wherein the processor is adapted to:

generate a first image patch from the central plane, wherein the first image patch has a first resolution;

generate a second image patch from the central plane, wherein the second image patch has a second resolution, lower than the first resolution;

extract a first feature map from the first image patch and a second feature map from the second image patch;

combine the first feature map with the second feature map; and generate an output layer based on the combined maps.

In an embodiment, the system comprises a display adapted to display the instruction to a user to acquire a 3D ultrasound image at a second position, wherein the instruction comprises a visual instruction.

In an embodiment, the system comprises an audio output device adapted to output the instruction to a user to acquire a 3D ultrasound image at a second position, wherein the instruction comprises an audible instruction.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
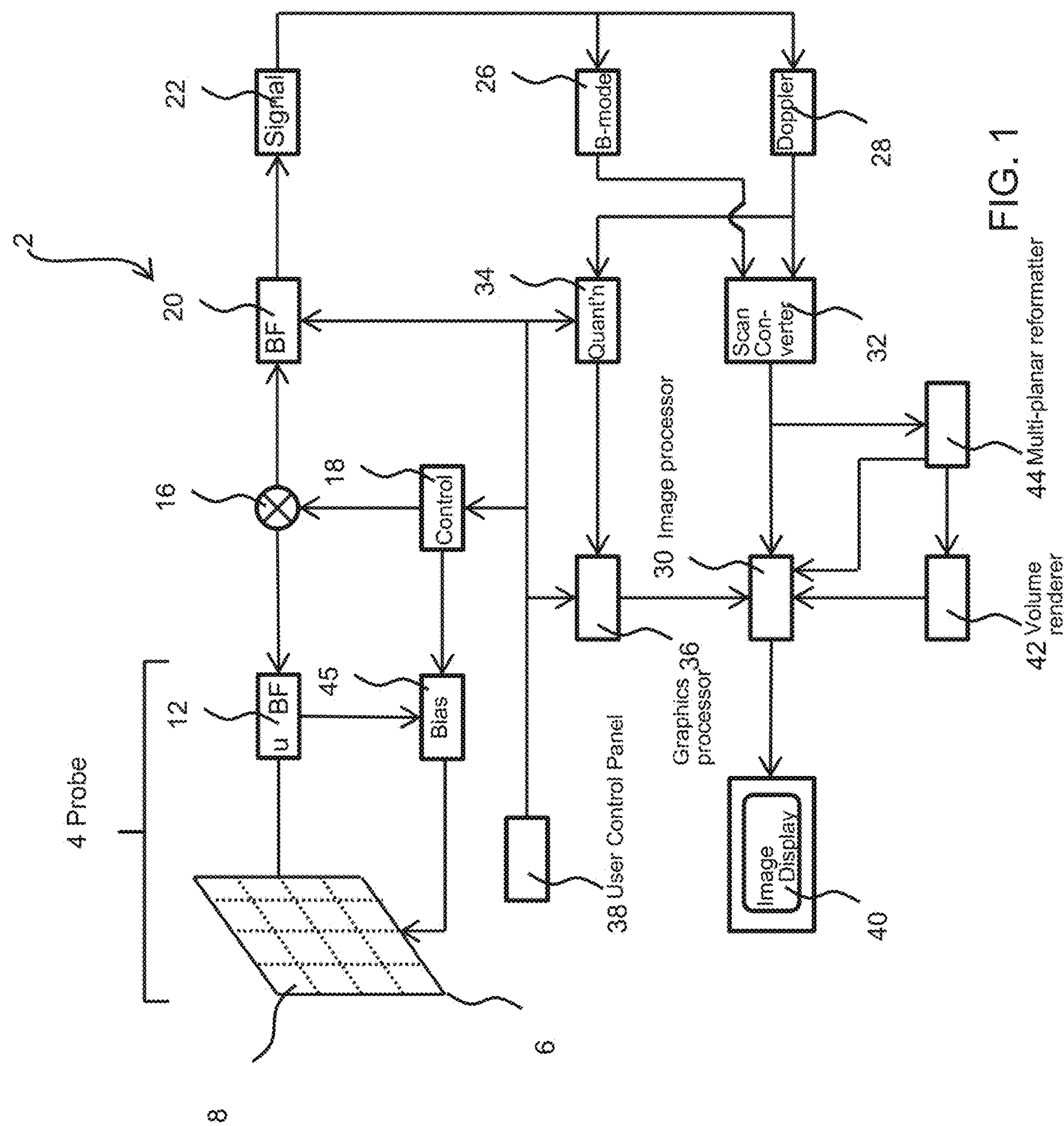
FIG. 1 shows an ultrasound diagnostic system to explain the operation.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a method for guiding the acquisition of an ultrasound image. A 3D ultrasound image is acquired by an ultrasound probe at a first position and an anatomical structure is identified within the 3D ultrasound image. A target imaging plane is estimated based on the identified anatomical structure and it is determined whether the target imaging plane is present within the 3D ultrasound image. If the target imaging plane is present, a displacement between a central plane of the 3D ultrasound image and the target plane is determined. If the displacement is below a predetermined threshold, the target imaging plane is extracted and if the displacement is above the predetermined threshold, an instruction to acquire a 3D ultrasound image with the ultrasound probe at a second position, different from the first position, is generated based on the displacement.

The invention further provides a method for estimating a target imaging plane. A central plane of a 3D ultrasound image is obtained, wherein the central plane contains at least part of an anatomical structure and a bounding box is generated around the anatomical structure. The bounding box is divided into a grid having a plurality of grid points and, for each grid point; an offset is estimated between the central plane and the target imaging plane. Finally, coordinates of the target imaging plane are estimated based on the offset for each grid point of the bounding box.

As the above method may be employed in an ultrasound imaging system, the general operation of an exemplary ultrasound system will first be described, with reference to FIG. 1, and with emphasis on the signal processing function of the system since this invention relates to the processing of the signals measured by the transducer array.

The system comprises an array transducer probe 4 which has a transducer array 6 for transmitting ultrasound waves and receiving echo information. The transducer array 6 may comprise CMUT transducers; piezoelectric transducers, formed of materials such as PZT or PVDF; or any other suitable transducer technology. In this example, the transducer array 6 is a two-dimensional array of transducers 8 capable of scanning either a 2D plane or a three dimensional volume of a region of interest. In another example, the transducer array may be a 1D array.

The transducer array 6 is coupled to a microbeamformer 12 which controls reception of signals by the transducer elements. Microbeamformers are capable of at least partial beamforming of the signals received by sub-arrays, generally referred to as "groups" or "patches", of transducers as described in U.S. Pat. No. 5,997,479 (Savord et al.), U.S. Pat. No. 6,013,032 (Savord), and U.S. Pat. No. 6,623,432 (Powers et al.).

It should be noted that the microbeamformer is entirely optional. Further, the system includes a transmit/receive (T/R) switch 16, which the microbeamformer 12 can be coupled to and which switches the array between transmission and reception modes, and protects the main beamformer 20 from high energy transmit signals in the case where a microbeamformer is not used and the transducer array is operated directly by the main system beamformer. The transmission of ultrasound beams from the transducer array 6 is directed by a transducer controller 18 coupled to the microbeamformer by the T/R switch 16 and a main transmission beamformer (not shown), which can receive input from the user's operation of the user interface or control panel 38. The controller 18 can include transmission circuitry arranged to drive the transducer elements of the array 6 (either directly or via a microbeamformer) during the transmission mode.

In a typical line-by-line imaging sequence, the beamforming system within the probe may operate as follows. During transmission, the beamformer (which may be the microbeamformer or the main system beamformer depending upon the implementation) activates the transducer array, or a sub-aperture of the transducer array. The sub-aperture may be a one dimensional line of transducers or a two dimensional patch of transducers within the larger array. In transmit mode, the focusing and steering of the ultrasound beam generated by the array, or a sub-aperture of the array, are controlled as described below. Upon receiving the backscattered echo signals from the subject, the received signals undergo receive beamforming (as described below), in order to align the received signals, and, in the case where a sub-aperture is being used, the sub-aperture is then shifted, for example by one transducer element. The shifted sub-aperture is then activated and the process repeated until all of the transducer elements of the transducer array have been activated.

For each line (or sub-aperture), the total received signal, used to form an associated line of the final ultrasound image, will be a sum of the voltage signals measured by the transducer elements of the given sub-aperture during the receive period. The resulting line signals, following the beamforming process below, are typically referred to as radio frequency (RF) data. Each line signal (RF data set) generated by the various sub-apertures then undergoes additional processing to generate the lines of the final ultrasound image. The change in amplitude of the line signal with time will contribute to the change in brightness of the ultrasound image with depth, wherein a high amplitude peak will correspond to a bright pixel (or collection of pixels) in the final image. A peak appearing near the beginning of the line signal will represent an echo from a shallow structure, whereas peaks appearing progressively later in the line signal will represent echoes from structures at increasing depths within the subject.

One of the functions controlled by the transducer controller 18 is the direction in which beams are steered and focused. Beams may be steered straight ahead from (orthogonal to) the transducer array, or at different angles for a wider field of view. The steering and focusing of the transmit beam may be controlled as a function of transducer element actuation time.

Two methods can be distinguished in general ultrasound data acquisition: plane wave imaging and "beam steered" imaging. The two methods are distinguished by a presence of the beamforming in the transmission ("beam steered" imaging) and/or reception modes (plane wave imaging and "beam steered" imaging).

Looking first to the focusing function, by activating all of the transducer elements at the same time, the transducer array generates a plane wave that diverges as it travels through the subject. In this case, the beam of ultrasonic waves remains unfocused. By introducing a position dependent time delay to the activation of the transducers, it is possible to cause the wave front of the beam to converge at a desired point, referred to as the focal zone. The focal zone is defined as the point at which the lateral beam width is less than half the transmit beam width. In this way, the lateral resolution of the final ultrasound image is improved.

For example, if the time delay causes the transducer elements to activate in a series, beginning with the outermost elements and finishing at the central element(s) of the transducer array, a focal zone would be formed at a given distance away from the probe, in line with the central element(s). The distance of the focal zone from the probe will vary depending on the time delay between each subsequent round of transducer element activations. After the beam passes the focal zone, it will begin to diverge, forming the far field imaging region. It should be noted that for focal zones located close to the transducer array, the ultrasound beam will diverge quickly in the far field leading to beam width artifacts in the final image. Typically, the near field, located between the transducer array and the focal zone, shows little detail due to the large overlap in ultrasound beams. Thus, varying the location of the focal zone can lead to significant changes in the quality of the final image.

It should be noted that, in transmit mode, only one focus may be defined unless the ultrasound image is divided into multiple focal zones (each of which may have a different transmit focus).

In addition, upon receiving the echo signals from within the subject, it is possible to perform the inverse of the above described process in order to perform receive focusing. In other words, the incoming signals may be received by the transducer elements and subject to an electronic time delay before being passed into the system for signal processing. The simplest example of this is referred to as delay-and-sum beamforming. It is possible to dynamically adjust the receive focusing of the transducer array as a function of time.

Looking now to the function of beam steering, through the correct application of time delays to the transducer elements it is possible to impart a desired angle on the ultrasound beam as it leaves the transducer array. For example, by activating a transducer on a first side of the transducer array followed by the remaining transducers in a sequence ending at the opposite side of the array, the wave front of the beam will be angled toward the second side. The size of the steering angle relative to the normal of the transducer array is dependent on the size of the time delay between subsequent transducer element activations.

Further, it is possible to focus a steered beam, wherein the total time delay applied to each transducer element is a sum of both the focusing and steering time delays. In this case, the transducer array is referred to as a phased array.

In case of the CMUT transducers, which require a DC bias voltage for their activation, the transducer controller 18 can be coupled to control a DC bias control 45 for the transducer array. The DC bias control 45 sets DC bias voltage(s) that are applied to the CMUT transducer elements.

For each transducer element of the transducer array, analog ultrasound signals, typically referred to as channel data, enter the system by way of the reception channel. In the reception channel, partially beamformed signals are produced from the channel data by the microbeamformer 12 and are then passed to a main receive beamformer 20 where the partially beamformed signals from individual patches of transducers are combined into a fully beamformed signal, referred to as radio frequency (RF) data. The beamforming performed at each stage may be carried out as described above, or may include additional functions. For example, the main beamformer 20 may have 128 channels, each of which receives a partially beamformed signal from a patch of dozens or hundreds of transducer elements. In this way, the signals received by thousands of transducers of a transducer array can contribute efficiently to a single beamformed signal.

The beamformed reception signals are coupled to a signal processor 22. The signal processor 22 can process the received echo signals in various ways, such as: band-pass filtering; decimation; I and Q component separation; and harmonic signal separation, which acts to separate linear and nonlinear signals so as to enable the identification of nonlinear (higher harmonics of the fundamental frequency) echo signals returned from tissue and micro-bubbles. The signal processor may also perform additional signal enhancement such as speckle reduction, signal compounding, and noise elimination. The band-pass filter in the signal processor can be a tracking filter, with its pass band sliding from a higher frequency band to a lower frequency band as echo signals are received from increasing depths, thereby rejecting noise at higher frequencies from greater depths that is typically devoid of anatomical information.

The beamformers for transmission and for reception are implemented in different hardware and can have different functions. Of course, the receiver beamformer is designed to take into account the characteristics of the transmission beamformer. In FIG. 1 only the receiver beamformers 12, 20 are shown, for simplicity. In the complete system, there will also be a transmission chain with a transmission micro beamformer, and a main transmission beamformer.

The function of the micro beamformer 12 is to provide an initial combination of signals in order to decrease the number of analog signal paths. This is typically performed in the analog domain.

The final beamforming is done in the main beamformer 20 and is typically after digitization.

The transmission and reception channels use the same transducer array 6 which has a fixed frequency band. However, the bandwidth that the transmission pulses occupy can vary depending on the transmission beamforming used. The reception channel can capture the whole transducer bandwidth (which is the classic approach) or, by using bandpass processing, it can extract only the bandwidth that contains the desired information (e.g. the harmonics of the main harmonic).

The RF signals may then be coupled to a B mode (i.e. brightness mode, or 2D imaging mode) processor 26 and a Doppler processor 28. The B mode processor 26 performs amplitude detection on the received ultrasound signal for the imaging of structures in the body, such as organ tissue and blood vessels. In the case of line-by-line imaging, each line (beam) is represented by an associated RF signal, the amplitude of which is used to generate a brightness value to be assigned to a pixel in the B mode image. The exact location of the pixel within the image is determined by the location of the associated amplitude measurement along the RF signal and the line (beam) number of the RF signal. B mode images of such structures may be formed in the harmonic or fundamental image mode, or a combination of both as described in U.S. Pat. No. 6,283,919 (Roundhill et al.) and U.S. Pat. No. 6,458,083 (Jago et al.) The Doppler processor 28 processes temporally distinct signals arising from tissue movement and blood flow for the detection of moving substances, such as the flow of blood cells in the image field. The Doppler processor 28 typically includes a wall filter with parameters set to pass or reject echoes returned from selected types of materials in the body.

The structural and motion signals produced by the B mode and Doppler processors are coupled to a scan converter 32 and a multi-planar reformatter 44. The scan converter 32 arranges the echo signals in the spatial relationship from which they were received in a desired image format. In other words, the scan converter acts to convert the RF data from a cylindrical coordinate system to a Cartesian coordinate system appropriate for displaying an ultrasound image on an image display 40. In the case of B mode imaging, the brightness of pixel at a given coordinate is proportional to the amplitude of the RF signal received from that location. For instance, the scan converter may arrange the echo signal into a two dimensional (2D) sector-shaped format, or a pyramidal three dimensional (3D) image. The scan converter can overlay a B mode structural image with colors corresponding to motion at points in the image field, where the Doppler-estimated velocities to produce a given color. The combined B mode structural image and color Doppler image depicts the motion of tissue and blood flow within the structural image field. The multi-planar reformatter will convert echoes that are received from points in a common plane in a volumetric region of the body into an ultrasound image of that plane, as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.).

The 2D or 3D images are coupled from the scan converter 32, multi-planar reformatter 44, and volume renderer 42 to an image processor 30 for further enhancement, buffering and temporary storage for display on an image display 40. The imaging processor may be adapted to remove certain imaging artifacts from the final ultrasound image, such as: acoustic shadowing, for example caused by a strong attenuator or refraction; posterior enhancement, for example caused by a weak attenuator; reverberation artifacts, for example where highly reflective tissue interfaces are located in close proximity; and so on. In addition, the image processor may be adapted to handle certain speckle reduction functions, in order to improve the contrast of the final ultrasound image.

In addition to being used for imaging, the blood flow values produced by the Doppler processor 28 and tissue structure information produced by the B mode processor 26 are coupled to a quantification processor 34. The quantification processor produces measures of different flow conditions such as the volume rate of blood flow in addition to structural measurements such as the sizes of organs and gestational age. The quantification processor may receive input from the user control panel 38, such as the point in the anatomy of an image where a measurement is to be made.

Output data from the quantification processor is coupled to a graphics processor 36 for the reproduction of measurement graphics and values with the image on the display 40, and for audio output from the display device 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as patient name. The user interface is also coupled to the transmit controller 18 to control the generation of ultrasound signals from the transducer array 6 and hence the images produced by the transducer array and the ultrasound system. The transmit control function of the controller 18 is only one of the functions performed. The controller 18 also takes account of the mode of operation (given by the user) and the corresponding required transmitter configuration and band-pass configuration in the receiver analog to digital converter. The controller 18 can be a state machine with fixed states.

The user interface is also coupled to the multi-planar reformatter 44 for selection and control of the planes of multiple multi-planar reformatted (MPR) images which may be used to perform quantified measures in the image field of the MPR images.

Figure 2:
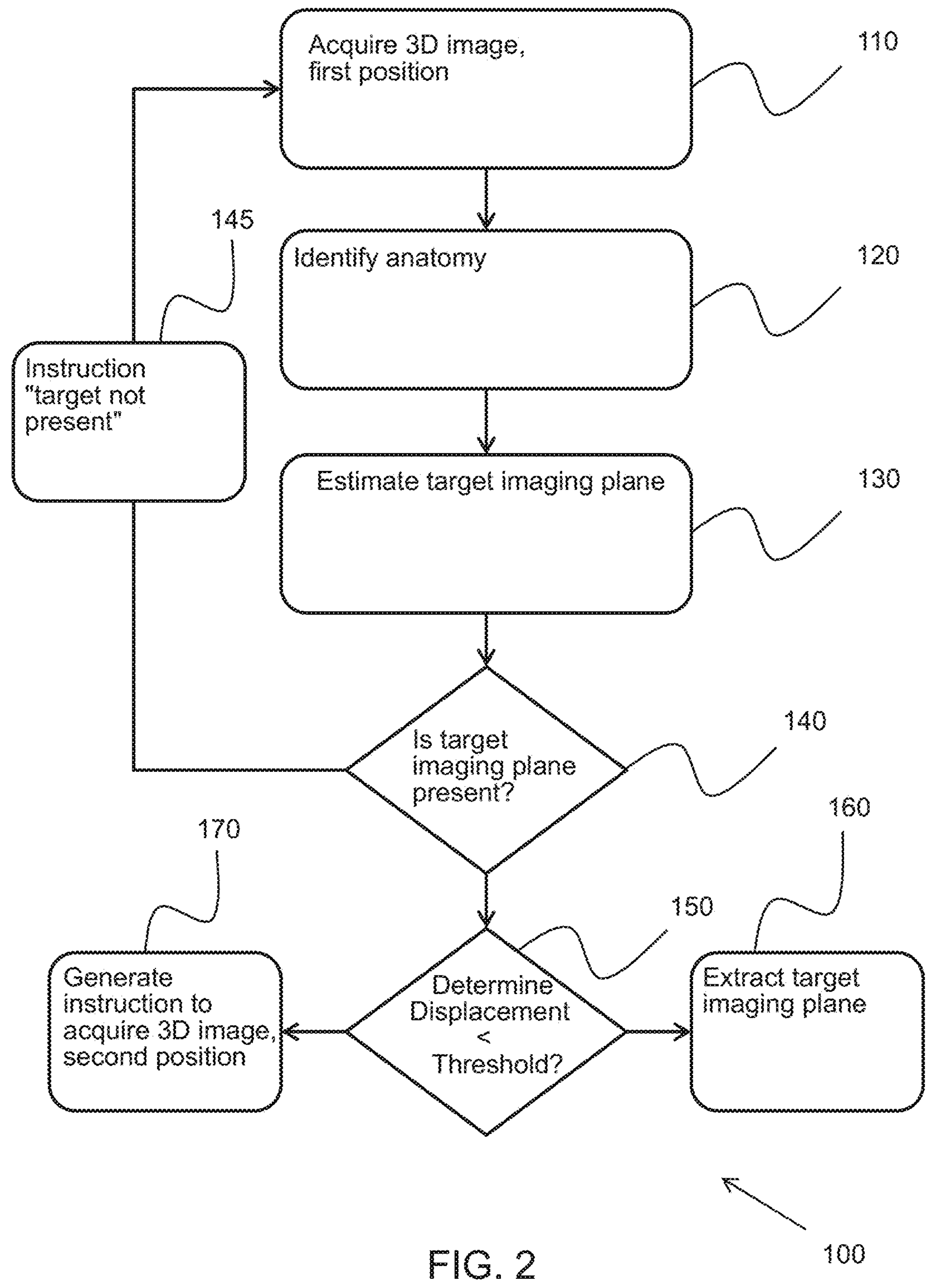
FIG. 2 shows a method of the invention.

FIG. 2 shows a method 100 for guiding the acquisition of an ultrasound image.

The method begins in step 110 where a 3D ultrasound image is acquired by controlling an ultrasound probe at a first position.

For example, an ultrasound exam may involve imaging a region of interest located at the first position. The region of interest may, for example, include an organ to be examined or a fetus.

In step 120, an anatomical structure is identified within the 3D ultrasound image.

The anatomical feature may include: an organ; an interior chamber of an organ, such as a ventricle of the heart; a skeletal structure; and a fetal structure, such as a fetal heart or stomach.

The anatomical structure may be identified by segmenting the anatomical structure. For example, automatic segmentation may be applied of structures of interest in fetal volume (e.g.: head, stomach, umbilical vein).

By way of example, a segmentation approach for the identifying the structure may be based on template deformation, using a template model of the shape of interest. Alternatively, another appropriate approach may make use of a UNET-based algorithm, based on deep learning and providing a mask of the organ to segment.

In other words, the anatomical structure may be identified within the 3D ultrasound image by way of machine learning based algorithms.

In step 130, a target imaging plane is determined based on the identified anatomical structure.

The determination of the target imaging plane may include the determination of a spatial coordinate system based on structures of interest. For example, the spatial coordinate system may be defined with reference to various organs, such as the heart, stomach and umbilical vein. These structures may be used in the extraction of the abdominal standard clinical plane; however, it is possible to utilize different structures to acquire other standard clinical planes, such as femur or head planes.

Figure 6:
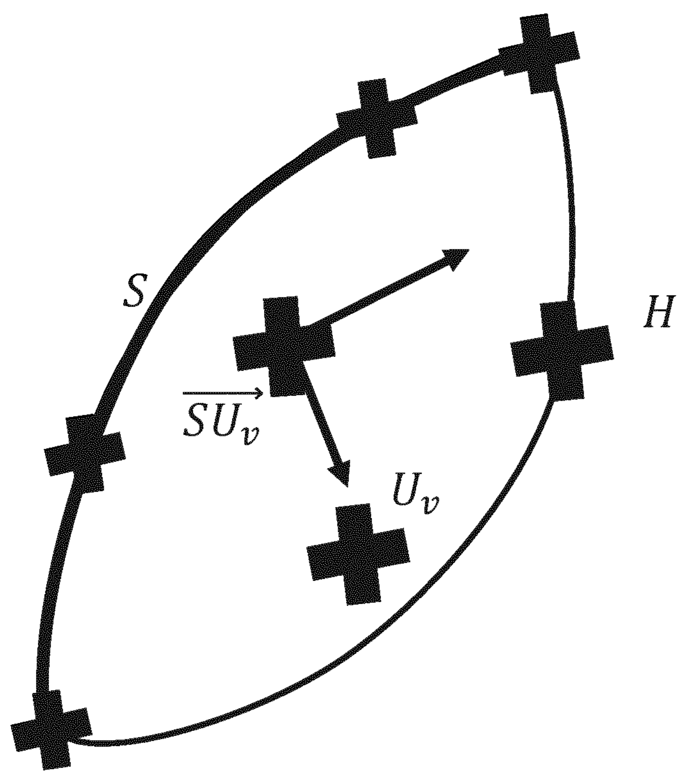
FIG. 6 shows an example of a schematic based instruction.

An example spatial coordinate system is described further below with reference to FIG. 6.

The extraction of the target imaging plane may be based on previously acquired knowledge, such as by user input or training of the system, of the position of the relevant plane in the defined coordinate system.

A method of determining the target imaging plane is discussed in further detail below with reference to FIG. 3.

In step 140, it is determined whether the target imaging plane is present within the acquired 3D ultrasound image.

The determining of the presence and position of the target imaging plane within the acquired 3D ultrasound image may be performed using a machine learning algorithm.

For example, once the target imaging plane is determined in step 130, the algorithm may determine whether said target imaging plane, or at least part of the target imaging plane, is within the volume of the acquired 3D ultrasound image.

If the target imaging plane is not present within the volume of the acquired 3D ultrasound image, the method may progress to step 145 where a message is presented to the user informing them that the target imaging plane is not present within the 3D ultrasound image. In this case, the method may then return to step 110 to acquire a different 3D ultrasound image containing at least part of the target imaging plane.

If the target imaging plane is present, the method progresses to step 150 where a displacement between a central plane of the 3D ultrasound image and the target imaging plane is determined. The displacement may include a translation and a rotation. In other words, the translation from the central plane to the target imaging plane is determined.

If the displacement is below a predetermined threshold, the method progresses to step 160 where the target imaging plane is extracted from the 3D ultrasound image. The predetermined threshold may represent a boundary within the 3D ultrasound image, meaning that if the displacement is below a predetermined threshold, the target imaging plane is fully contained within the volume of the 3D ultrasound image. In other words, the maximum amplitude of the displacement should be smaller than a given fraction, or threshold value, of the volume dimensions of the 3D ultrasound image in each direction. Alternatively, the predetermined threshold may be defined based on a distance and/or an angle between the target imaging plane and the central plane.

In other words, when the user acquires a 3D ultrasound image that is analyzed as being close to the target imaging plane, a signal may be provided to the user, indicating the target imaging plane extraction can be performed from the 3d ultrasound image at the current probe location.

Returning to step 150, if the displacement is found to be above the predetermined threshold the method progresses to step 170. In step 170, and instruction to acquire a 3D ultrasound image with the ultrasound probe at a second position, different from the first position, is generated based on the displacement. The instruction may take the form of a visual instruction or an audible instruction.

For example, if the target imaging plane is within the volume of the 3D ultrasound image but not close enough to the central slice (i.e. outside of the predetermined threshold) a user instruction may be generated. The threshold may be set to any suitable number for locating the target imaging plane within the 3D ultrasound image. The threshold may trigger when a value above the threshold is detected. Alternatively, the threshold may trigger when a value below the threshold is detected.

The user instruction may present a proposed probe movement to obtain the target imaging plane in the center of the subsequently acquired 3D ultrasound image. In the example of a visual instruction, the user may be guided by way of a schematic based instruction or a 3D volume based instruction.

The schematic based instruction may include a schematic drawing showing the current position of the ultrasound probe. The schematic drawing may also include a proposed motion of the probe in the form of arrows for translation and rotation in order to acquire a 3D ultrasound image including the target imaging plane.

The 3D volume based instruction may comprise a direct volume rendering of the acquired 3D ultrasound image with a motion guidance overlay. The motion guidance overlay may include arrows for translation and rotation of the ultrasound probe.

Following the movement of the ultrasound probe according to the provided instructions, the method may return to step 140 and proceed as described above to step 160, wherein the target imaging plane is acquired.

Following the acquisition of the target imaging plane, the method may further include performing biometric analysis on the acquired target imaging plane. As the target imaging plane is typically selected for use in a clinical process, a biometric measurement may be performed automatically on the acquired target imaging plane.

Figure 3:
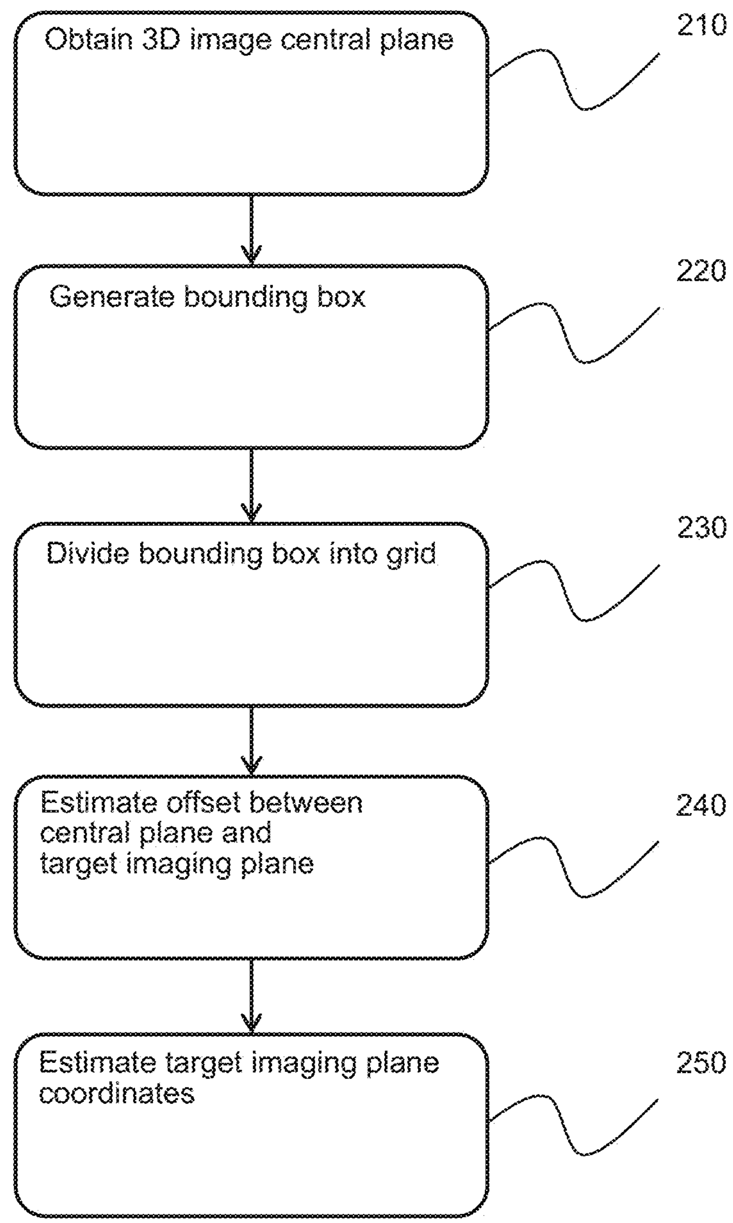
FIG. 3 shows a further method of the invention.

FIG. 3 shows the step 130 of determining the target imaging plane in more detail.

In step 210, a central plane of the 3D ultrasound image is obtained, wherein the central plane contains at least part of the anatomical structure.

As described above, the user navigates an ultrasound probe to a structure of interest to acquire the 3D ultrasound image, such that the 3D ultrasound image contains at least part of the anatomical structure.

For example, the central plane of the 3D ultrasound (which may, in some circumstances, be acquired by way of multi-planar reconstruction, MPR) may contain the anatomical structure. By way of a specific example, for a fetal abdominal circumference measurement, an approximately orthogonal cut through the abdomen may be contained in the central plane.

In step 220, a bounding box is generated around the anatomical structure in the central plane.

There are several methods available for performing bounding box detection in 2D images, such as the central plane of the 3D ultrasound image. For example, the method described in Joseph Redmon et al, YOLO9000: Better, Faster, Stronger, CVPR 2018 may be used. Further, several pre-trained models for computer vision problems such as this are available meaning that transfer learning may be employed to address body part detection, and in particular fetal body part detection, as described in Pan, S. J et al, A survey on transfer learning. IEEE Trans Knowl Data Eng, 22(10), 1345-1359, 2009.

In step 230, the bounding box is divided into a grid having a plurality of grid points. The bounding box may be divided into any N×N grid, wherein N may be varied according to the resolution required by the application.

For example, two points $b^{start}$ and $b^{end}$ are may be used to define the smallest square in the central pane that includes the bounding box about the anatomical structure. This square is then subdivided into a grid of N×N cells with center point coordinates $g_{xy}$.

In step 240, an offset between the central plane and the target imaging plane (e.g. an optimal imaging plane) is estimated for each grid point.

For each grid point $g_{xy}$, an offset $o_{xy}$ from the central plane to the optimal imaging plane is estimated, for example using a multi-resolution convolutional neural network as described below.

In step 250, the coordinates of the target imaging plane are estimated based on the offset for each grid point of the bounding box.

By interpolating $g_{xy}+o_{xy}$ using a linear regression, the target geometry of the target imaging plane can be estimated.

The estimation of the offset may include applying a multi-resolution neural network to the central plane. A multi-resolution neural network is trained to estimate an offset vector $o_{xy}:=(0,0,o_{xy})^T$ for each grid point that indicates the distance to the target imaging plane.

Multi-resolution neural networks have been shown to yield accurate results for several segmentation tasks in medical imaging as discussed in Schmidt-Richberg et al.: Abdomen Segmentation in 3D Fetal Ultrasound Using CNN-powered Deformable Models, MICCAI Workshop on Fetal and Infant Imaging (FIFI 2017) and Brosch, T. et al, Foveal fully convolutional nets for multi-organ segmentation. Proc. SPIE, 105740U, 2018.

The general idea of a multi-resolution neural network is to combine image patches of different resolution for pixel-wise classification. On each resolution level, image features are extracted using standard convolutional layers. Then, feature maps of coarse levels are successively up-sampled and combined with the next finer level. In this way, segmentations of the original image resolution are obtained while having a large perspective field to take extensive image context into account. Alternative machine learning approaches may be considered. However, neural networks produce accurate results for complex learning tasks such as these whilst also being capable of producing almost real-time performance.

In this case, this general concept is employed for plane regression, where a multi-resolution network is trained such that the final output layer of size N×N×1 holds the offsets $o_{xy}$. However, as the offset layer has a much smaller resolution than the original ultrasound image, a down-sampling rather than up-sampling strategy is used.

Figure 9:
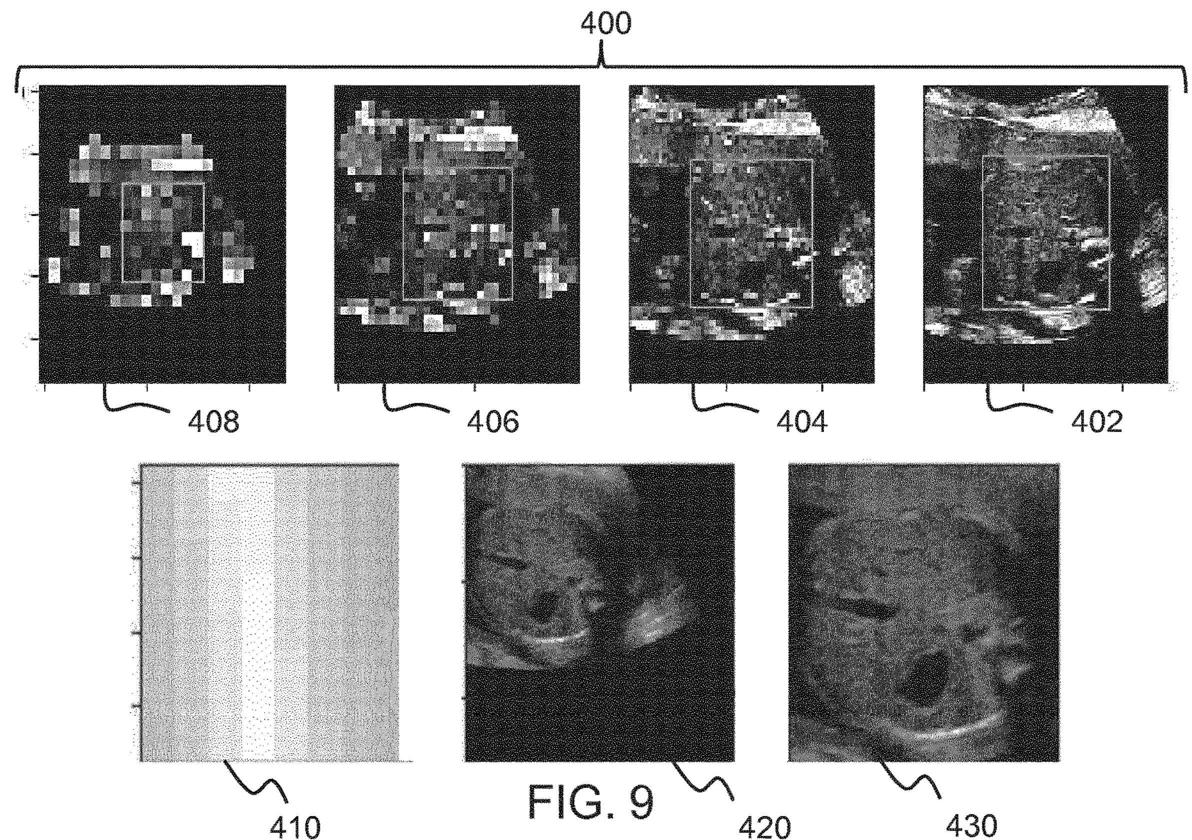
FIG. 9 shows examples of the input patches for the levels of the network shown in FIG. 8.
Figure 10:
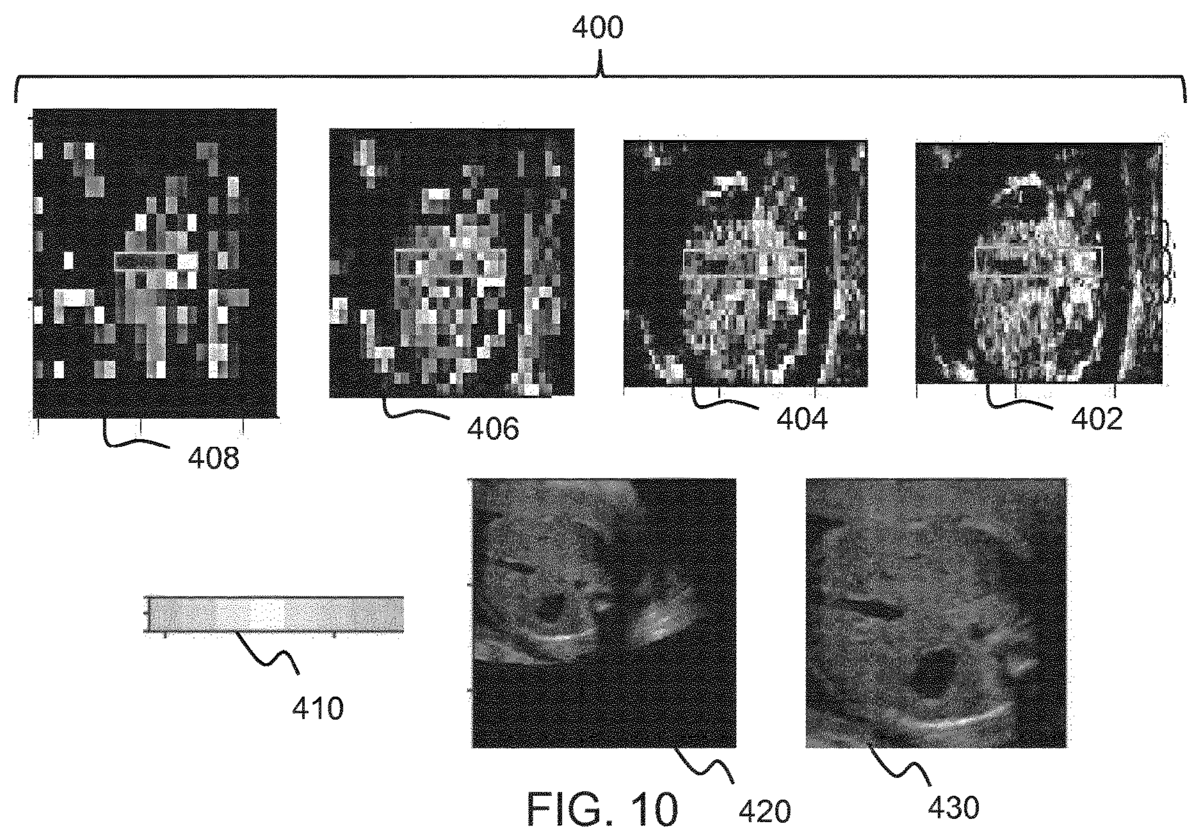
FIG. 10 shows further examples of the input patches for the levels of the network shown in FIG. 8.

This means, instead of up-sampling coarse levels and combining them with finer levels as in a typical multi-resolution neural network architecture, fine levels are successively down-sampled and combined with coarser levels. This network architecture is detailed further in FIG. 8 and examples for the corresponding image patches are shown in FIGS. 9 and 10.

The network can be trained with the mean squared difference between a ground truth, annotated by a user, and the estimated offsets as loss function.

Figure 4A:
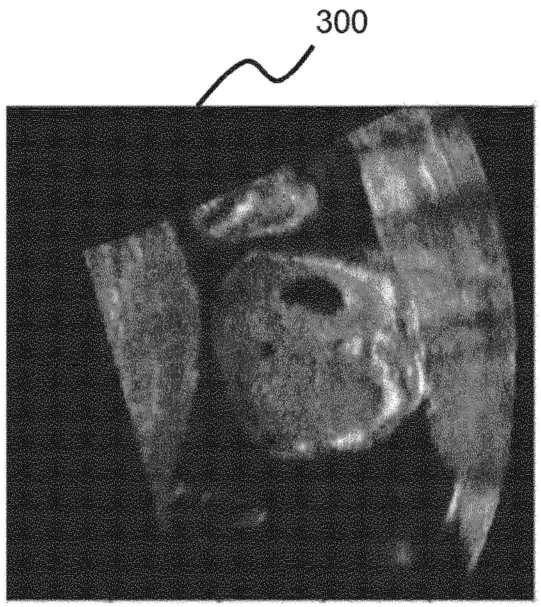
FIGS. 4A and 4B show a comparison between automatically extracted imaging planes and expertly annotated imaging planes.
Figure 4A:
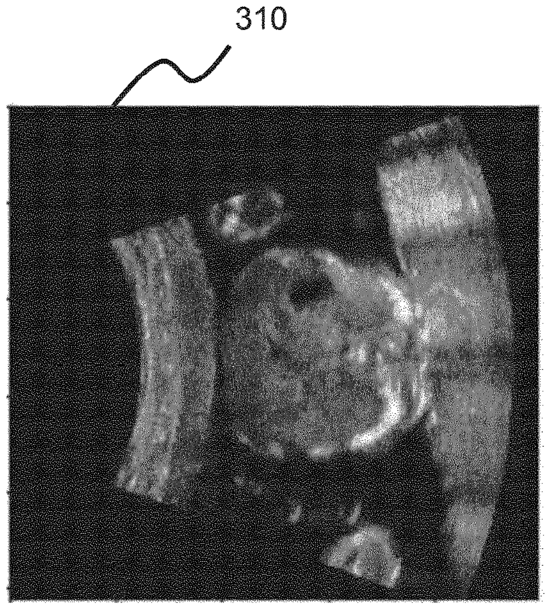
Figure 4B:
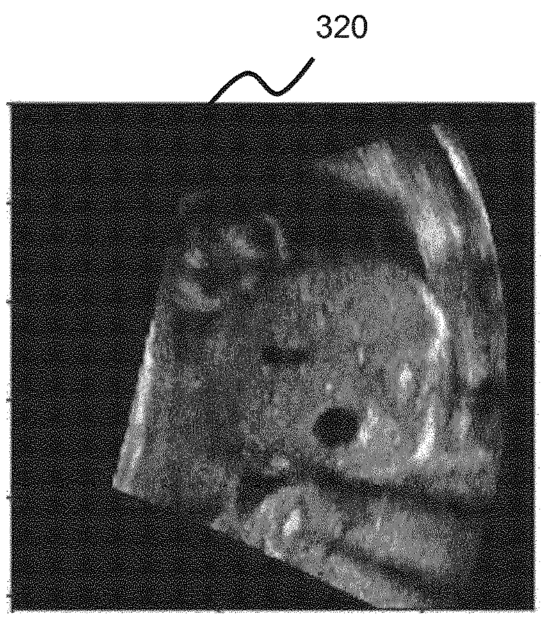
Figure 4B:
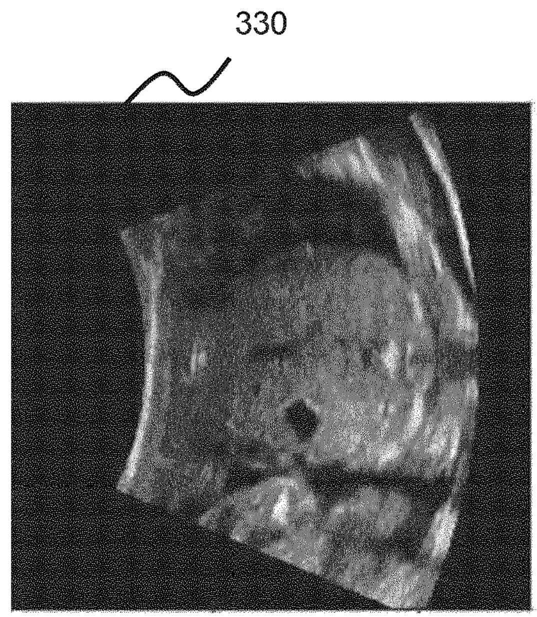

FIGS. 4A and 4B show a comparison between automatically extracted planes 300 and 320, extracted according to the methods detailed above, and expertly annotated planes 310 and 330, respectively. In both cases, it is clear to see that the performance of the automatic extraction of the target imaging plane is comparable to the expertly annotated image planes.

Figure 5:
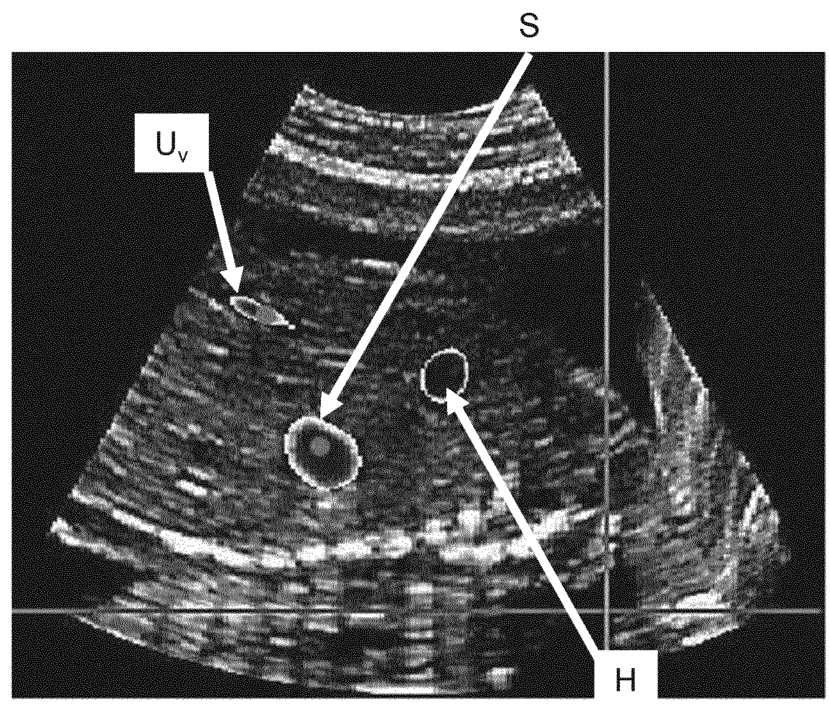
FIG. 5 shows a segmentation result for identifying an anatomical structure.

FIG. 5 shows the result of an automatic segmentation of various anatomical structures. In this Figure, a heart H, stomach S and umbilical vein Uv are shown following segmentation with a deep learning algorithm. FIG. 6 shows an example of a schematic based instruction, which defines a spatial reference coordinate system based on the segmented anatomical landmarks (heart: H, stomach: S, umbilical vein: Uv) as shown in FIG. 5. The schematic based instruction may further include translation and rotation instructions, informing the user how to move the ultrasound probe.

Figure 7:
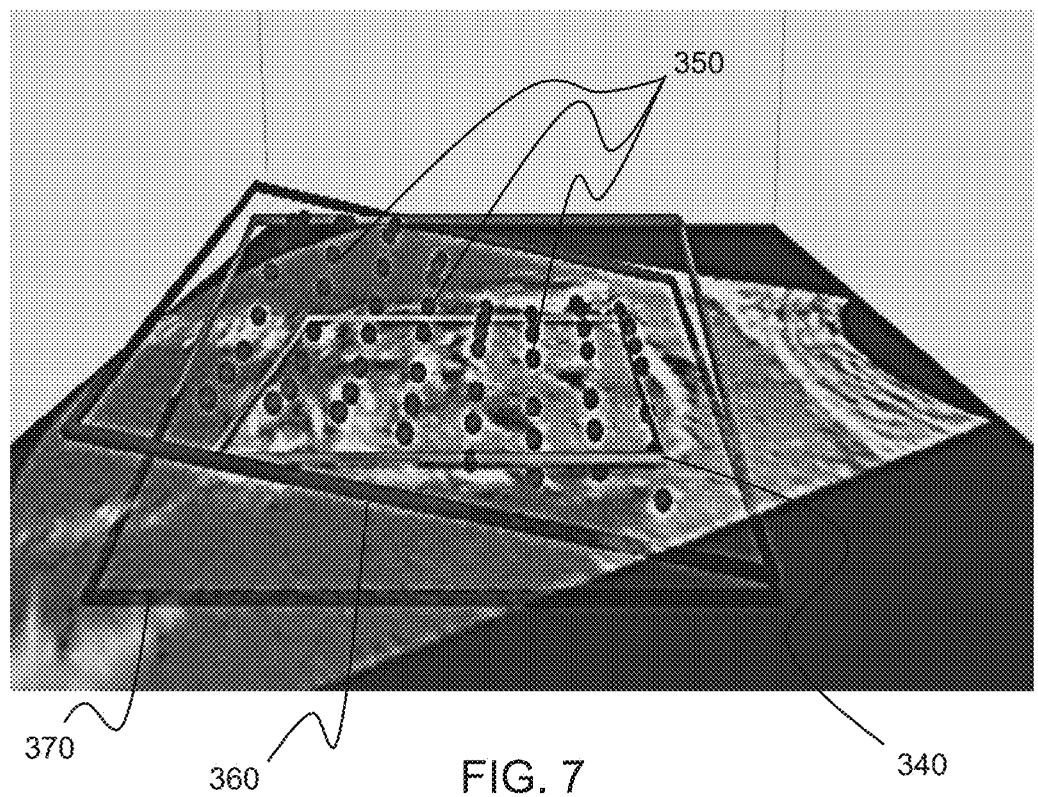
FIG. 7 shows a visualization of estimating a target imaging plane.

FIG. 7 shows a visualization of the approach for estimating the target imaging plane described above with reference to FIG. 3, wherein the anatomical structure is the torso of a fetus. The central box 340 marks the bounding box around the fetal torso in the center slice of the 3D image. The points 350 indicate the displaced grid points $g_{xy}+o_{xy}$, where the offsets $o_{xy}$ are automatically estimated using a multi-resolution neural network. By interpolation of these points, the target imaging plane 360 is determined using linear regression. The final box 370 shows the ground truth annotation of the target imaging plane.

Figure 8:
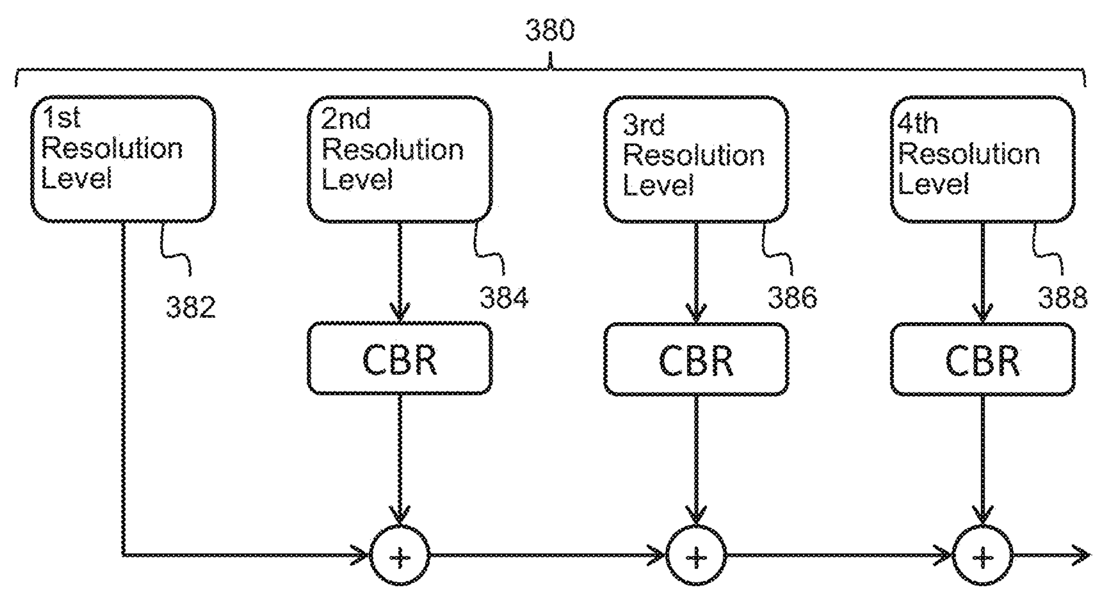
FIG. 8 shows a schematic representation of a multi-resolution convolutional regression network.

FIG. 8 shows a schematic representation of an example architecture of a multi-resolution convolutional regression network with 4 resolution levels 380 and N=8. Each rounded box stands for one or multiple operational layers, where CBR indicates a block consisting of non-padded convolution (C) with a given kernel size, batch normalization (B) and ReLU activation (R).

The first resolution level 382 will receive an image patch with the highest available resolution, such as the central plane of the 3D ultrasound. As described above, the multi-resolution neural network operates a series of downsampling layers in order to generate the output layer. Thus, the second 384, third 386 and fourth 388 resolution layers receive image patches, each having a sequentially lower resolution. In other words, the image patches are downsampled and combined for each resolution layer.

FIGS. 9 and 10 show examples of the input image patches 400 of all four levels of the network shown in FIG. 8. The patches are shown for x/y axis (FIG. 9) and x/z axis (FIG. 10). The grey box in each input patch corresponds to the extent of the output layer.

More specifically, the first image patch 402, having the highest resolution is supplied to the first resolution level. Similarly, the second image patch 404 is supplied to the second resolution level, the third image patch 406 is supplied to the third resolution level and the fourth image patch 408 is supplied to the fourth resolution level.

The output layer of the multi-resolution neural network following the processing of the input image patches 400 is shown by the offset grid 410. The offset grid represents the offsets required for each grid point of the bounding box to reach the target imaging plane, wherein the darker the shade of a grid square, the greater the offset.

Image 420 represents a ground truth view plane 420, which is a previously annotated target imaging plane as identified by a user. Image 430 shows the ground truth plane resampled within the torso bounding box, represented as the grey square in the input image patches.

As mentioned above the invention provides a guiding method as well as a method of estimating a target imaging plane. The latter comprises:

acquiring a 3D ultrasound image;

identifying an anatomical structure within the 3D ultrasound image;

obtaining a central plane of the 3D ultrasound image, wherein the central plane contains at least part of the anatomical structure;

generating a bounding box around the anatomical structure in the central plane;

dividing the bounding box into a grid having a plurality of grid points;

for each grid point of the plurality of grid points, estimating an offset between the central plane and the target imaging plane (e.g., an optimal imaging plane); and estimating coordinates of the target imaging plane based on the offset for each grid point of the bounding box.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method for guiding the acquisition of an ultrasound image, the method comprising:

acquiring a 3D ultrasound image by controlling an ultrasound probe at a first position;

identifying an anatomical structure within the 3D ultrasound image;

estimating a target imaging plane based on the identified anatomical structure;

determining that the target imaging plane is present within the 3D ultrasound image;

determining a displacement between a central plane of the 3D ultrasound image and the target plane; and if the displacement is below a predetermined threshold, extracting the target imaging plane from the 3D ultrasound image; or if the displacement is above the predetermined threshold, generating an instruction to acquire another 3D ultrasound image with the ultrasound probe at a second position, different from the first positon, based on the displacement.

2. A method as claimed in claim 1, wherein the estimation of the target imaging plane comprises:

obtaining the central plane of the 3D ultrasound image, wherein the central plane contains at least part of the anatomical structure;

generating a bounding box around the anatomical structure in the central plane;

dividing the bounding box into a grid having a plurality of grid points;

for each grid point of the plurality of grid points, estimating an offset between the central plane and the target imaging plane; and estimating coordinates of the target imaging plane based on the offset for each grid point of the bounding box.

3. A method as claimed in claim 2, wherein the estimation of the offset comprises applying a multi-resolution neural network to the central plane.

4. A method as claimed in claim 3, wherein the applying of the multi-resolution neural network comprises:

generating a first image patch from the central plane, wherein the first image patch has a first resolution;

generating a second image patch from the central plane, wherein the second image patch has a second resolution, lower than the first resolution;

extracting a first feature map from the first image patch and a second feature map from the second image patch;

combining the first feature map with the second feature map; and generating an output layer based on the combined maps, wherein the output layer comprises the offset for each grid point.

5. A method as claimed in claim 1, wherein the identifying of the anatomical structure comprises segmenting the anatomical structure.

6. A method as claimed in claim 1, wherein the displacement comprises one or more of:

a translation; and a rotation.

7. A method as claimed in claim 1, wherein the instruction comprises one or more of:

a visual instruction; and an audible instruction.

8. A method as claimed in claim 7, wherein the visual instruction comprises one or more of:

a schematic based instruction; and a 3D volume based instruction.

9. A method as claimed in claim 1, wherein the method further comprises performing biometric analysis on the acquired target imaging plane.

10. A computer program product implemented in a non-transitory computer readable medium, comprising computer program code means which is adapted, when said computer program product is run on an ultrasound imaging system, to implement the method of claim 1.

11. An ultrasound imaging system, the system comprising:

an ultrasound probe adapted to acquire a 3D ultrasound image when located at a first position;

a processor, wherein the processor is adapted to:

identify an anatomical structure within the 3D ultrasound image;

estimate a target imaging plane based on the identified anatomical structure;

determine if the target imaging plane is present within the 3D ultrasound image;

if the target imaging plane is present, determine a displacement between a central plane of the 3D ultrasound image and the target plane; and if the displacement is below a predetermined threshold, extract the target imaging plane from the 3D ultrasound image; or if the displacement is above the predetermined threshold, generate an instruction to acquire another 3D ultrasound image with the ultrasound probe at a second position, different from the first positon, based on the displacement.

12. A system as claimed in claim 11, wherein the processor is further adapted to:

obtain the central plane of the 3D ultrasound image, wherein the central plane contains at least part of the anatomical structure;

generate a bounding box around the anatomical structure in the central plane;

divide the bounding box into a grid having a plurality of grid points;

for each grid point of the plurality of grid points, estimate an offset between the central plane and the target imaging plane; and estimate coordinates of the target imaging plane based on the offset for each grid point of the bounding box.

13. A system as claimed in claim 12, wherein the processor is further adapted to apply a multi-resolution neural network to the central plane, wherein the processor is adapted to:

generate a first image patch from the central plane, wherein the first image patch has a first resolution;

generate a second image patch from the central plane, wherein the second image patch has a second resolution, lower than the first resolution;

extract a first feature map from the first image patch and a second feature map from the second image patch;

combine the first feature map with the second feature map; and generate an output layer based on the combined maps.

14. A system as claimed in claim 11, wherein the system comprises a display adapted to display the instruction to a user to acquire the another 3D ultrasound image at the second position, wherein the instruction comprises a visual instruction.

15. A system as claimed in claim 11, wherein the system comprises an audio output device adapted to output the instruction to a user to acquire the another 3D ultrasound image at the second position, wherein the instruction comprises an audible instruction.

* * * * *